United States Patent
Behringer et al.

[19]

[11] Patent Number: 5,902,096
[45] Date of Patent: *May 11, 1999

[54] DIAPHRAGM PUMP HAVING MULTIPLE RIGID LAYERS WITH INLET AND OUTLET CHECK VALVES

[75] Inventors: Bruce E. Behringer, Park Ridge, N.J.; James A. Mawhirt, Brooklyn, N.Y.

[73] Assignee: Bayer Corporation, Tarrytown, N.Y.

[*] Notice: This patent is subject to a terminal disclaimer.

[21] Appl. No.: 08/800,103

[22] Filed: Feb. 13, 1997

Related U.S. Application Data

[63] Continuation of application No. 08/549,958, Oct. 30, 1995, Pat. No. 5,669,764, which is a continuation-in-part of application No. 08/319,856, Oct. 7, 1994, abandoned, and application No. 08/319,858, Oct. 7, 1994, abandoned.

[51] Int. Cl.[6] ............................................ F04B 43/073
[52] U.S. Cl. ................. 417/395; 417/566; 417/DIG. 1
[58] Field of Search ............................. 417/395, DIG. 1

[56] References Cited

U.S. PATENT DOCUMENTS

| | | | |
|---|---|---|---|
| 588,296 | 8/1897 | Spencer | 417/395 |
| 996,588 | 6/1911 | Kennedy | 137/846 |
| 1,282,075 | 10/1918 | Hand | 137/846 |
| 2,821,930 | 2/1958 | Smith | 417/395 |
| 2,871,795 | 2/1959 | Smith | 92/98 R |
| 3,000,320 | 9/1961 | Ring | 417/395 X |
| 3,010,404 | 11/1961 | Anderson | 417/395 |
| 3,093,086 | 6/1963 | Altoz et al. | 417/395 |
| 3,155,110 | 11/1964 | Hoffman | 137/846 |

(List continued on next page.)

FOREIGN PATENT DOCUMENTS

| | | |
|---|---|---|
| AV 72473/87 | 12/1987 | Australia . |
| 982874 | 2/1976 | Canada . |
| 2311239 | 12/1976 | France . |
| 3209643 | 9/1983 | Germany . |
| 503039 | 2/1976 | U.S.S.R. . |
| 389075 | 6/1931 | United Kingdom . |
| WO 92/00476 | 1/1992 | WIPO . |
| WO 96/35876 | 11/1996 | WIPO . |

OTHER PUBLICATIONS

Pump Handbook (Karassik et al.) 1976 McGraw–Hill p. 10–232 FIG. 3 & p. 10–233.
European Search Report for Application No. EP 95 11 5032.
English language abstract for DE 3209643.
Modern Plastics Encyclopedia '92, p. 11, McGraw Hill, 1991.
Processes and Materials of Manufacture 2nd Edition, Roy A. Lindberg, p. 114, Allyn and Bacon, Inc., 1978.

*Primary Examiner*—Timothy Thorpe
*Assistant Examiner*—Cheryl J. Tyler
*Attorney, Agent, or Firm*—Orrick, Herrington & Sutcliffe LLP

[57] ABSTRACT

An integral valve diaphragm pump has a first rigid layer, a second rigid layer and a flexible membrane therebetween. Concave surfaces in the two rigid layers form a pump. The pump includes an actuating chamber which is alternately connected to a source of pressure and a source of vacuum. A pump chamber is connected to a fluid source and a fluid receiver through a filling check valve and a dispensing check valve, respectively. Duckbill and spring loaded ball check valves are disclosed.

18 Claims, 3 Drawing Sheets

U.S. PATENT DOCUMENTS

| | | |
|---|---|---|
| 3,176,714 | 4/1965 | Smith et al. . |
| 3,232,524 | 2/1966 | Rice et al. .............................. 417/395 |
| 3,307,481 | 3/1967 | De Castelet ........................... 417/395 |
| 3,324,877 | 6/1967 | Bochan ................................... 137/846 |
| 3,652,187 | 3/1972 | Loeffler et al. ....................... 417/393 |
| 3,741,687 | 6/1973 | Nystroem ............................... 417/395 |
| 3,844,529 | 10/1974 | Brandt, Jr. et al. . |
| 3,881,513 | 5/1975 | Chang . |
| 4,072,164 | 2/1978 | Kaden . |
| 4,084,606 | 4/1978 | Mittleman .............................. 137/846 |
| 4,265,600 | 5/1981 | Mandroian ........................ 417/395 X |
| 4,304,257 | 12/1981 | Webster . |
| 4,355,653 | 10/1982 | Credle, Jr. . |
| 4,390,325 | 6/1983 | Elo et al. ................................ 417/395 |
| 4,410,322 | 10/1983 | Archibald .............................. 417/478 |
| 4,430,048 | 2/1984 | Fritsch . |
| 4,516,604 | 5/1985 | Taplin . |
| 4,583,920 | 4/1986 | Lindner .................................. 417/395 |
| 4,848,722 | 7/1989 | Webster . |
| 4,852,851 | 8/1989 | Webster . |
| 4,858,883 | 8/1989 | Webster . |
| 4,875,956 | 10/1989 | Brackett . |
| 4,944,659 | 7/1990 | Labbe et al. .......................... 417/332 |
| 4,981,157 | 1/1991 | Denkinger . |
| 5,387,395 | 2/1995 | Coassin ................................. 137/846 |

DIAPHRAGM PUMP HAVING MULTIPLE RIGID LAYERS WITH INLET AND OUTLET CHECK VALVES

This is a continuation of application Ser. No. 08/549,958 filed on Oct. 30, 1995, now U.S. Pat. No. 5,669,764, which is a continuation-in-part of application Ser. No. 08/319,856, filed on Oct. 7, 1994, now abandoned, and a continuation-in-part of application Ser. No. 08/319,858, filed on Oct. 7, 1994, now abandoned.

BACKGROUND OF THE INVENTION

The present invention relates to an integral valve diaphragm pump and method of pumping.

Small volume and precision pumps are known in the art; however, these pumps involve complex structures which are difficult to manufacture and are expensive.

SUMMARY OF THE INVENTION

The main object of the present invention is to eliminate the disadvantages of prior art precision volume pumps and methods.

Another object of the present invention is to integrate the valve function into a small single unit and to separate the actuation air system from the fluid system with a gasket type flexible membrane.

Another object of the present invention is to provide an all-pneumatic precision pump with passive valving.

Another object of the invention is to provide a diaphragm pump with improved volumetric pumping precision.

These and other objects and advantages of the present invention are achieved in accordance with the present invention by a pump having a flexible membrane separating a pump chamber and an actuator chamber. The diaphragm pump is pneumatic, with a filling check valve and a dispensing check valve passively responding to line pressures created by the diaphragm pump. Valve cavities containing the check valves are connected through a common connection to the pump chamber. The check valves passively control filling and dispensing flow into and out of the pump chamber.

In accordance with the invention, the integral valve diaphragm pump has a first rigid layer having a substantially planar first surface, a second rigid layer having a substantially planar second surface. The first and second rigid layers are connected in superposition with the flexible membrane therebetween and in contact with the first and second surfaces. The flexible membrane is partially compressed between the first and second layers.

A filling check valve is oriented to permit flow from a fluid source into the pump. A dispensing check valve is oriented to permit flow out of the pump into a fluid receiver. The pump comprises an actuating chamber demarcated by a first concave surface in the first surface and one side of the flexible membrane, and a pump chamber demarcated by a second concave surface in the second surface and the other side of the flexible membrane.

In one embodiment, the second rigid layer has a substantially planar third surface parallel to the second surface. A third rigid layer having a substantially planar fourth surface is connected to the second rigid layer, with the third and fourth surfaces superposed. The filling check valve is a duckbill valve disposed in a cavity in the third surface, and the dispensing check valve is a duckbill valve disposed in a cavity in the fourth surface. The filling check valve is located opposite the pump chamber in the second rigid layer, with a first passageway connecting the two. A second passageway connects the dispensing valve with the first passageway.

In accordance with the method of the invention, the pump is operated by first applying a vacuum to the actuating chamber to flex the flexible membrane against the first concave surface. This opens the filling check valve and closes the dispensing check valve, and fills the pump chamber with fluid through the filling check valve. A pressure is then applied to the actuating chamber, flexing the membrane against the second concave surface. This closes the filling check valve and opens the dispensing check valve, dispensing the fluid from the pump chamber through the dispensing valve to a fluid receiver.

In another embodiment of the present invention, the filling and dispensing check valves for controlling inflow and outflow to the pump chamber are spring loaded ball check valves. In yet another embodiment, both duckbill and spring loaded check valves can be used.

In each of the embodiments, the rigid layers are preferably acrylic plastic material, which are preferably clear. The layers may be connected by bolts. Alternatively, the layers may be connected by diffusion, adhesive or solvent bonding as set forth in U.S. Pat. No. 4,875,956, the disclosure of which is hereby incorporated by reference.

The pump in accordance with the present invention is preferably used in unified fluid circuits for clinical diagnostic analyzers for hematology, chemistry and immunology. Such uses include pumping various reagents into a chamber for performing a test on a sample.

These and other features of the present invention will be described in more detail in the following detailed description taken with the attached drawings wherein:

DETAILED DESCRIPTION OF THE INVENTION

Figure 1:
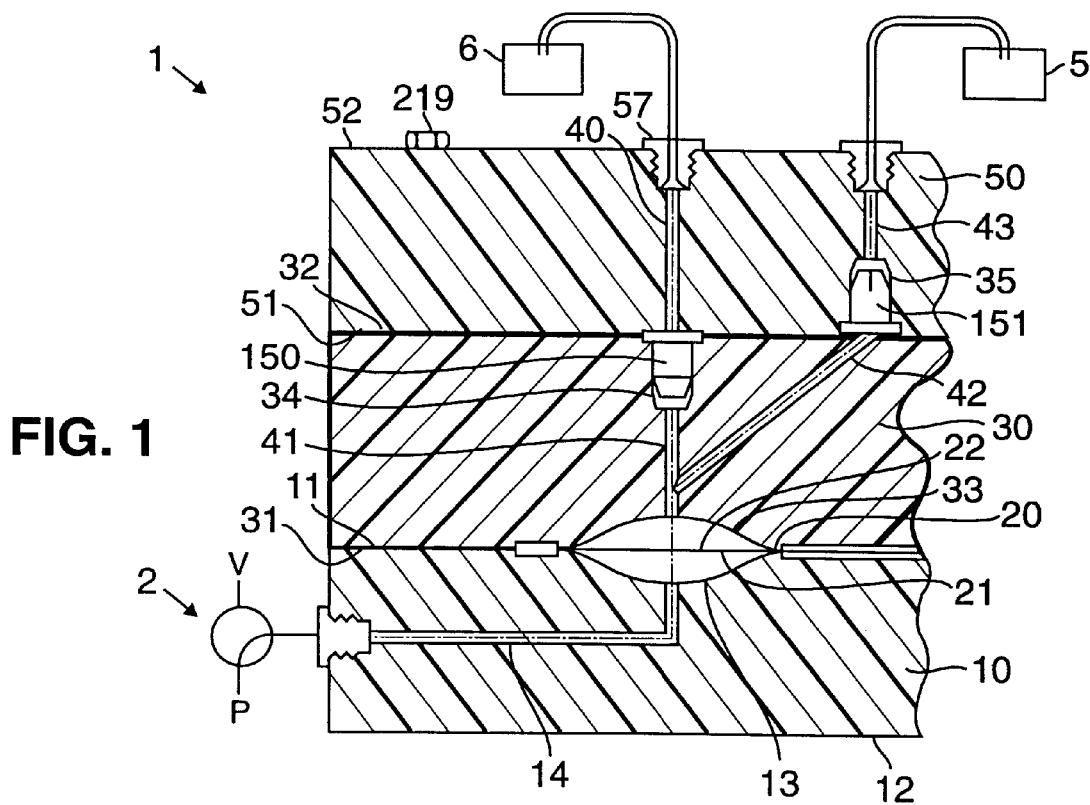
FIG. 1 is a sectional view of a pump according to the present invention.

Referring to FIG. 1, the diaphragm pump 1 has a first rigid layer 10 having substantially planar surfaces 11, 12, and a second rigid layer 30 having substantially planar surfaces 31, 32. The first layer 10 and second layer 30 are connected so that surfaces 11, 31 are superposed. A flexible membrane layer 20 disposed therebetween. A third rigid layer 50 having substantially planar surfaces 51, 52 is connected to the second rigid layer so that surfaces 32, 51 are superposed.

The first rigid layer 10 has an actuating passageway 14 for receiving either pressure P or vacuum V from a three-way solenoid valve 2. The passageway 14 opens into concave surface 13 in surface 11. Concave surface 13 forms an actuating chamber with side 21 of flexible membrane 20.

The second rigid layer 30 has a concave surface 33 in the surface 31, forming a pump chamber with side 22 of the flexible membrane 20. A first fluid passageway 41 extends through the rigid layer 30 from the center of the concave surface 33 in a direction normal to the surface 31. The passageway 41 extends to a filling check valve chamber 34, which may be located within layer 30, as shown in FIG. 1. A one-way filling check valve 150 is disposed within the chamber 34 in an orientation permitting flow only in a direction into the pump chamber. A passageway 40 extends from the surface 51 proximate the filling check valve chamber 34, through the rigid layer 50, to a fluid source 6.

It is preferred that the filling check valve 150 is placed as close as possible to the pump chamber, minimizing the length of passageway 41. This reduces pump inaccuracy caused by the compressibility of air or other gas that may become trapped in the passageway 41.

A second fluid passageway 42 extends at an oblique angle from surface 32 through the rigid layer 30 to communicate with the first passageway 41. The second passageway 42 is thereby in fluid communication with the pump chamber through the first passageway 41. Alternatively, the second passageway 42 could communicate directly with the pump chamber. The passageway 42 extends to a dispensing check valve chamber 35, which may be located within layer 50, as shown in FIG. 1. A one-way dispensing check valve 151 is disposed within the chamber 35 in an orientation permitting flow only in a direction out of the pump chamber. A passageway 43 extends from the dispensing valve chamber 35, through rigid layer 50, to a fluid receiver 5.

Figure 2:
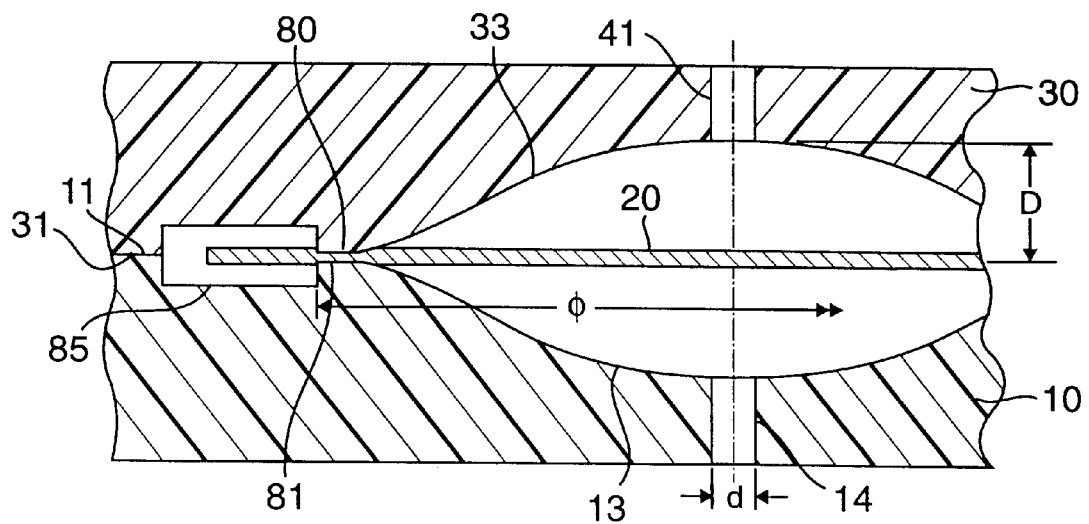
FIG. 2 is a sectional view of the flexible membrane and other components of the pump of FIG. 1.

The structure shown in FIG. 1 completely separates the fluid pumping side of the pump from the actuator side by the sealing of the flexible membrane 20 between the layer 10 and the layer 30. Compression of the flexible membrane 20 between the layer 10 and layer 30 must be closely controlled for proper functioning of the pump. If the membrane is too tightly compressed, it wrinkles or puckers, and so does not properly comply to the shape of the concave surfaces 13, 33, adversely affecting pump precision. If the membrane is not compressed sufficiently between the layers 10, 30, leakage of the fluid between the layers may occur. FIG. 2 is an enlarged partial sectional view of the pump, showing the membrane and concave surfaces. By controlling the depth of the compression lands 80, 81 from the surfaces 11, 31 during the manufacturing process, proper compression of the flexible membrane 20 is maintained. In a currently preferred embodiment of the invention, a silicon rubber flexible membrane 0.010" thick in its free state is compressed a total of 22% nominally, with, manufacturing tolerances permitting a range of 8% to 53% compression. Other configurations will be apparent to those skilled in the art. A relief volume 85 is provided in the layers 10, 30 outside the compression lands for extruded membrane material.

The actuating pressure and vacuum applied through passageway 14 results in a force on the flexible membrane 20 tending to extrude the membrane into the passageways 14, 41. This can change the pump volume and degrade pump precision. The extrusion effect may be reduced for a given membrane material by minimizing diameter d of the passageways 14, 41 at their junctions with the concave surfaces, while still providing sufficient cross sectional flow area. In a currently preferred embodiment using a flexible membrane of 0.010" thick silicon rubber, the diameter d is between 0.58 mm and 1.05 mm.

The depth D of the concave surfaces 13, 33 must be selected to provide a sufficient pumping volume while permitting the flexible membrane 20 to seal without puckering or leaving pockets. An optimum depth D is a function of the diameter Ø of the pump chamber and the actuating chamber. In the currently preferred embodiment having a pump chamber diameter Ø between 14 and 27 mm, the ratio of depth D to diameter Ø is between 11 and 14 percent.

Figure 3:
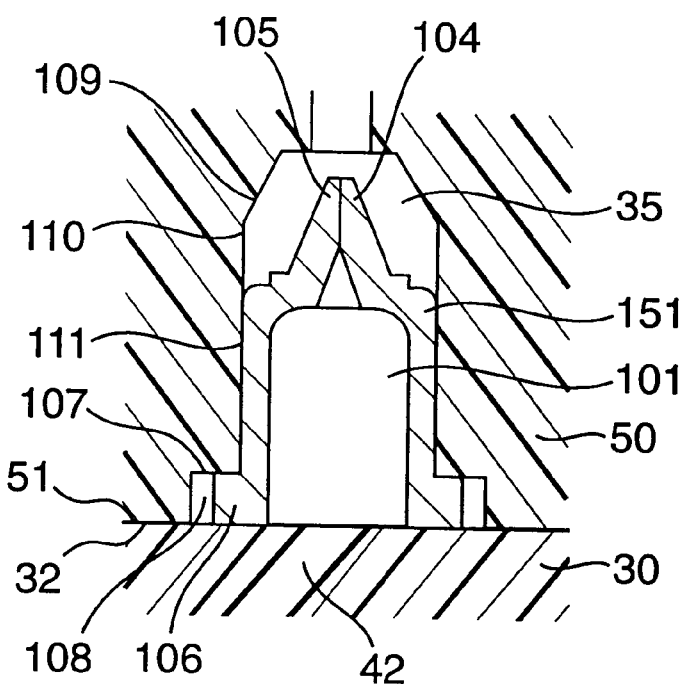
FIG. 3 is a sectional view of the check valve and other components of the pump of FIG. 1.

In the preferred embodiment shown in FIG. 1, the filling check valve 150 and the dispensing check valve 151 are duckbill type check valves. The valves 150, 151 are shown in FIG. 1 in different rotational orientations 90° apart; the actual orientation does not affect valve performance. FIG. 3 is an enlarged cross-sectional view of a duckbill check valve 103 as installed in the dispensing valve chamber 35. Chamber 34 has similar features. The duckbill valve 103 has a central bore 101 and a duckbill closure comprising deformable members 104, 105. The diameter 111 of the valve fits within diameter 110 of the valve chamber 35.

The valve 103 is installed in the chamber 35 before assembling the rigid layers 30, 50. The chamber 35 has a counterbore 108 for receiving a lip 106 of the valve. The lip 106 is compressed between a shoulder 107 of the counterbore and the surface 51, forming a pressure-tight seal. This integral seal permits the layers 30, 50 to be bolted together without bonding the surfaces 51, 32 and without separately sealing the passageway at these surfaces. The layers 30, 50, however, can alternatively be connected by diffusion, adhesive or solvent bonding after first inserting the duckbill devices in the valve chambers.

The chamber 35 has a taper 109 at its outlet end. The tapered outlet end reduces the "dead volume," or non-circulating volume of fluid, in the part of the chamber surrounding the deformable members 104, 105 of the duckbill. It is believed the taper also streamlines flow through the chamber. These improvements advantageously reduce the amount of air trapped in this area to facilitate pump priming.

The duckbill check valve remains closed in the absence of a pressure differential. When the pressure on the inlet side of the valve exceeds the pressure on the outlet (duckbill) side by a small cracking pressure, the deformable members 104, 105 separate, permitting flow through the valve. A pressure differential in the opposite direction closes the deformable members 104, 105, preventing backflow. The cracking pressure is dependent on the structure of the duckbill device itself. In a current embodiment of the pump, a duckbill valve marketed by Vernay Laboratories Inc., Cat. #VA-3426, fabricated from Viton® or silicone rubber, is used.

Figure 4:
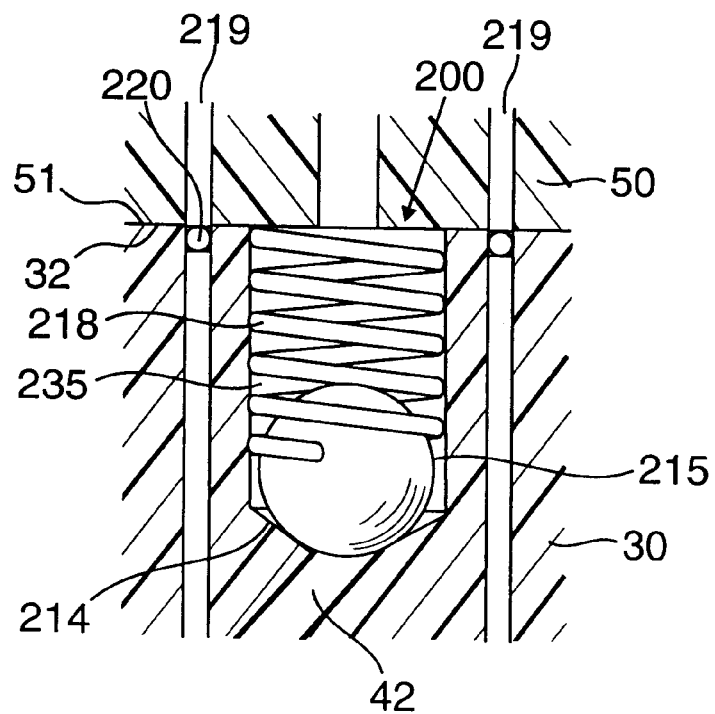
FIG. 4 is a sectional view of an alternative check valve and other components of a pump according to the present invention.

In another embodiment of the invention, one or both of the filling check valve 150 and dispensing check valve 151 are spring-loaded ball check valves. FIG. 4 is an enlarged cross-sectional view of a spring-loaded ball check valve 200 as installed in a dispensing valve chamber 235. A valve seat 214 is formed in the valve chamber 235. A ball 215 is urged into sealing contact with the valve seat 214 by a compression spring 218. The spring 218 is preloaded against the surface 32 during assembly of layers 30, 50. When the pressure in the passageway 42 exceeds a cracking pressure, the spring 218 is overcome and the ball 215 moves off the seat 214, permitting flow through the valve. A reverse pressure differential across the valve, that is, a differential with the greater pressure being on the output side of the valve, works in conjunction with the spring to more firmly seat the ball.

The cracking pressure of the ball check valve is the inlet pressure at which the ball 215 will move off the valve seat 214 and allow flow. This occurs when the force on the inlet side of the ball exceeds force on the outlet side. The force on the inlet side in the closed position is a function of the inlet pressure and the circular area of the ball exposed to the inlet pressure; this can be expressed by the equation:

$$F_i = P_i A_i$$

where $F_i$ is the force from the inlet side, $P_i$ is the pressure at the inlet port, and $A_i$ is the area of the ball exposed to the inlet pressure.

The force from the outlet side is a function of the outlet pressure and the force of the spring on the rigid device. This can be expressed by the equation:

$$F_o = F_s + P_o A_i$$

where $F_o$ is the force from the outlet side, $F_s$ is the force from the compression spring, $P_o$ is the pressure at the outlet port, and $A_i$ is the area of the ball exposed to the inlet pressure.

From the above equations, it is apparent that several physical design variables can be varied independently in order to get the flow characteristics desired in the valve. Element 215 can have a shape other than spherical and still be subject to the same equations.

The back pressure that can be tolerated by the ball check valve from flow in the reverse direction is relatively high and is limited only by the strength of the ball structure itself.

The rigid layers 30, 50 can be connected together by diffusion, adhesive or solvent bonding after inserting the ball 215 and compression spring 218 into the valve chamber 235. Alternatively, the two rigid layers may be bolted together. When the layers are bolted, it is preferred that a provision for sealing, such as O-ring 220, be provided.

Other types of check valve devices can be used herein, although the described check valve devices are particularly advantageous in view of the fact that they are particularly suited to a unified fluidics circuit of the type shown.

The operation of the pump will be described with regard to FIGS. 5A–5D, which show a schematic representation of the solenoid valve 2, the pump 1 with flexible membrane 20, and check valves 150, 151. The check valves 150, 151 may be duckbill check valves, ball check valves, or other check valves. Similar element numbers are used where possible to show similar elements from other figures.

Figure 5A:
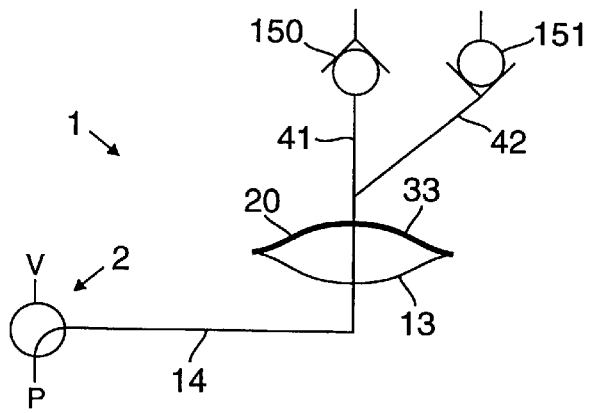
FIGS. 5A–5D are schematic diagrams showing the steps in the method according to the present invention using the pump of FIG. 1.
Figure 5B:
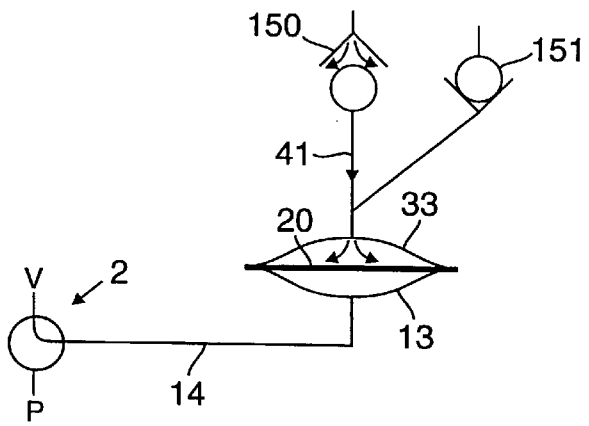

In an initial state, the flexible membrane 20 is in the position shown in FIG. 5A. The actuating chamber is pressurized through passageway 14 using solenoid valve 2. The flexible membrane 20 is pressed against the concave surface 33. Because there is no fluid flow through passageways 41, 42, the check valves 150, 151 remain in a closed position. To operate the valve, a vacuum is first applied to the actuating chamber through passageway 14 using solenoid valve 2, as shown in FIG. 5B. The flexible membrane 20 moves through an intake stroke from its position against concave surface 33 to a position against concave surface 13. The resulting increase in volume of the pump chamber causes a pressure drop across the check valves 150, 151. The filling check valve 150, which is oriented for flow into the pump chamber, opens and permits flow from the fluid source 6 through passageway 41 to the pump chamber. The dispensing check valve 151, oriented for flow away from the pump chamber, is closed tightly by the greater pressure on its outlet side.

Figure 5C:
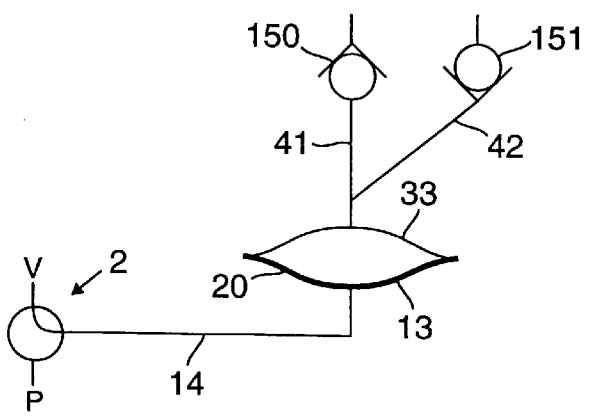

The flexible membrane 20 completes its intake stroke in the position shown in FIG. 5C, pressed against the concave surface 13. In this position, there is no fluid flow through the check valves, and both check valves 150, 151 are closed. A precise volume of fluid is contained in the pump chamber as defined by the concave surface 33 and the flexible membrane 20 pressed against concave surface 13.

Figure 5D:
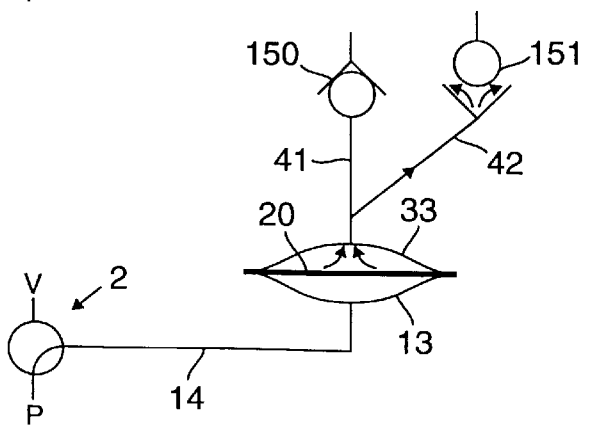

To exhaust the pump, pressure is applied to the actuating chamber through passageway 14 using solenoid valve 2, as shown in FIG. 5D. The flexible membrane 20 moves through an exhaust stroke from its position against concave surface 13 to a position against concave surface 33. The resulting decrease in volume of the pump chamber increases the pressure on the pump side of the check valves 150, 151. The dispensing check valve 151 is opened by the pressure on its input side, permitting flow from the pump chamber through passageway 42 to the fluid receiver (FIG. 1). The filling check valve 150 is closed tightly by the pressure on its outlet side. At the end of the exhaust stroke, the diaphragm pump is in position to begin a new pumping cycle.

The volume of fluid dispensed during a pumping cycle is a precise function of the volume enclosed by the concave surfaces 13, 33. Because the volume of fluid displaced by the check valves undergoes relatively little change between the open and closed positions, the volumetric precision of the pump is not greatly affected by these components.

In one embodiment of the present invention, the rigid layers are composed of fully normalized clear cast acrylic and the flexible membrane is composed of silicone sheeting. Each of the rigid layers is about 0.250" to 1.000" thick. The flexible membrane is silicon rubber about 0.010" thick. The fluid passageways have a diameter of about 0.020" to 0.040" and the concave surfaces have a spherical radius of 0.500" to 0.750" and a diameter of 0.375" to 1.125" with a depth of 0.060" to 0.140".

It is understood that the embodiments described hereinabove are merely illustrative and are not intended to limit the scope of the invention. It is realized that various changes, alterations, rearrangements and modifications can be made by those skilled in the art without substantially departing from the spirit and scope of the present invention.

What is claimed is:

1. An integral valve diaphragm pump comprising:
   a first rigid layer having a substantially planar first surface;
   a second rigid layer having a substantially planar second surface and a substantially planar third surface opposite said second surface;
   a flexible membrane;
   the first and second rigid layers being connected in superposition with the flexible membrane therebetween and in contact with the first and second surfaces;
   an actuating chamber located in the first rigid layer demarcated by a first concave surface in the first surface and one side of the flexible membrane;
   a pump chamber located in the second layer demarcated by a second concave surface in the second surface and the other side of the flexible membrane;
   a first fluid passageway connected to the pump chamber and having a filling check valve therein;
   a second fluid passageway connected to the pump chamber having a dispensing check valve therein;
   a third fluid passageway connected to the actuating chamber at a first junction;
   a pressure source and a vacuum source connected to the actuating chamber through the third fluid passageway operative to flex the flexible membrane between the first and second concave surfaces; and
   a third rigid layer having a substantially planar fourth surface, said second and third rigid layers being connected in superposition at said third and fourth surfaces;
   wherein said filling check valve is disposed in a first chamber in said second rigid layer or said third rigid layer and said dispensing check valve is disposed in a second chamber in said second rigid layer or said third rigid layer.

2. The pump according to claim 1, wherein the first and second rigid layers comprise acrylic plastic.

3. The pump according to claim 1, wherein the first and second rigid layers connected in superposition are bolted together.

4. The pump according to claim 1, wherein each of the filling check valve and the dispensing check valve is a ball check valve.

5. The pump according to claim 1, wherein each of the filling check valve and the dispensing check valve is a duckbill check valve.

6. The pump according to claim 1, wherein the first fluid passageway and the second fluid passageway are connected to the pump chamber through a common passageway at a second junction.

7. The pump according to claim 6, wherein the second concave surface has a depth from the second surface, the pump chamber further comprises a diameter at the second surface, and the depth of the second concave surface is between 11 and 14 percent of the diameter of the pump chamber.

8. The pump according to claim 6, wherein the second rigid layer further comprises a substantially planar third surface opposite said second surface; and said filling check valve is located proximate said third surface opposite said pump chamber.

9. The pump according to claim 8, wherein said dispensing check valve is proximate said third surface.

10. The pump according to claim 9, wherein the first, second and third rigid layers are acrylic plastic.

11. The pump according to claim 10, wherein the first, second and third rigid layers are fused together.

12. The pump according to claim 9, wherein the first, second and third rigid layers are bolted together.

13. The pump according to claim 9, wherein said check valves are duckbill check valves.

14. The pump according to claim 9, wherein said check valves are ball check valves.

15. The pump according to claim 1, wherein the flexible membrane comprises a silicon rubber membrane having a free-state thickness and the silicon rubber membrane is compressed between the first and second rigid layers so as to reduce its free-state thickness by between 8 and 53 percent.

16. The pump according to claim 1, wherein the first fluid passageway and the second fluid passageway are connected to a common passageway at a second junction, and the common passageway, but not the second passageway, is connected to the pump chamber.

17. An integral valve diaphragm pump comprising:

a first rigid layer having a substantially planar first surface;

a second rigid layer having a substantially planar second surface;

a flexible membrane;

the first and second rigid layers being connected in superposition with the flexible membrane therebetween and in contact with the first and second surfaces;

an actuating chamber located in the first rigid layer demarcated by a first concave surface in the first surface and one side of the flexible membrane;

a pump chamber located in the second layer demarcated by a second concave surface in the second surface and the other side of the flexible membrane;

a first fluid passageway connected to the pump chamber and having a filling check valve therein;

a second fluid passageway connected to the pump chamber having a dispensing check valve therein;

a third fluid passageway connected to the actuating chamber at a first junction; and a pressure source and a vacuum source connected to the actuating chamber through the third fluid passageway operative to flex the flexible membrane between the first and second concave surfaces, wherein the first concave surface has a depth from the first surface, the actuating chamber further comprises a diameter at the first surface, and the depth of the first concave surface is between 11 and 14 percent of the diameter of the actuating chamber.

18. A method of pumping precise amounts of fluid between a fluid source and a fluid receiver, comprising the steps of:

providing a diaphragm pump comprising a flexible membrane mounted between and in contact with a first surface on a first rigid layer and a second surface on a second rigid layer, an actuating chamber in the first rigid layer demarcated by a first concave surface in the first surface and one side of the flexible membrane, a pump chamber in the second layer demarcated by a second concave surface in the second rigid layer and the other side of the flexible membrane, and a third rigid layer superposed on said second rigid layer;

applying a vacuum to the actuating chamber;

filling the pump chamber from a fluid source through a one-way filling valve in a first chamber in said second rigid layer or said third rigid layer;

terminating the application of the vacuum;

applying pressure to the actuating chamber; and dispensing the volume of fluid to a fluid receiver through a one-way dispensing valve in a second chamber in said second rigid layer or said third rigid layer.

* * * * *